(12) United States Patent
Ulyanenkov et al.

(10) Patent No.: US 7,110,492 B2
(45) Date of Patent: Sep. 19, 2006

(54) METHOD OF DETERMINING PARAMETERS OF A SAMPLE BY X-RAY SCATTERING APPLYING AN EXTENDED GENETIC ALGORITHM INCLUDING A MOVEMENT OPERATOR

(75) Inventors: Alex Ulyanenkov, Karlsruhe (DE); Stanislaw Sobolewski, Minsk (BY)

(73) Assignee: Bruker AXS GmbH, Karlsruhe (DE)

( * ) Notice: Subject to any disclaimer, the term of this patent is extended or adjusted under 35 U.S.C. 154(b) by 44 days.

(21) Appl. No.: 10/952,800

(22) Filed: Sep. 30, 2004

(65) Prior Publication Data

US 2005/0074090 A1 Apr. 7, 2005

(30) Foreign Application Priority Data

Oct. 7, 2003 (EP) .................................. 03022421

(51) Int. Cl.
*G01N 23/201* (2006.01)
(52) U.S. Cl. ....................................................... 378/86
(58) Field of Classification Search ................ 378/70, 378/86, 88, 87, 90
See application file for complete search history.

(56) References Cited

U.S. PATENT DOCUMENTS 6,192,103 B1 * 2/2001 Wormington et al. ......... 378/73
6,823,043 B1 * 11/2004 Fewster et al. ............... 378/86

OTHER PUBLICATIONS

Ghoshray, S; Yen, K.K; "More efficient genetic algorithm for solving optimization problems" 1995, IEEE Conference on Systems, Man and Cybernetics—vol. 5, pp. 4515-4520.*

Ulyanenkov A. et al.: "Genetic algorithm: Refinement of X-ray reflectivity data from multilayers and thin films" 6th International Conference on Surface X-Ray and Neutron Scattering (SXNS-6) ; Noordwijkerhout, Neth Sep. 12-Sep. 17, 1999, vol. 283, No. 1, Sep. 12, 1999, pp. 237-241, XP002269236 Phys B. Condens Matter; Physica B: Condensed Matter 2000 Elsevier Science Publishers B.V., Amsterdam, Netherlands *p. 237-p. 238*.

Pan Wang et al.: "Study on a novel hybrid adaptive genetic algorithm embedding conjugate gradient algorithm" Proceedings of the Third World Congress of Intelligent Control and Automation, vol. 1, Jun. 28, 2000-Jul. 2, 2000, pp. 630-633, XP010505285 China *p. 630-p. 632*.

(Continued)

*Primary Examiner*—Courtney Thomas
(74) *Attorney, Agent, or Firm*—Paul Vincent

(57) ABSTRACT

A method of determining parameters of a sample by X-ray scattering comprising the steps of exposing the sample to X-rays and measuring scattered X-ray intensity, generating a parameterized model of the sample which is used for numerical simulation of scattered X-ray intensity on the basis of a physical scattering theory, comparing the experimental and simulated X-ray scattering data to generate an error value, and modifying the parameters of the model by means of a genetic algorithm involving an amount of individuals each with an equal number N of encoded parameters forming a generation and applying the genetic operators of "selection", "crossover" and "mutation" used for composing successive generations of evolving individuals, is characterized in that from one generation to the next a "movement" genetic operator is applied which moves at least some of the encoded parameters of at least some of the individuals towards the respective encoded parameters of the individual with the smallest error value. The inventive method improves the genetic algorithm such that it can approximate the true sample parameters faster and with better reliability.

8 Claims, 8 Drawing Sheets

OTHER PUBLICATIONS

Prahlada-Rao B B et al.: "A genetic algorithm for channel routing using inter-cluster mutation" Evolutionary Computation, 1994. IEEE World Congress on Computational Intelligence, Proceedings of the First IEEE Conference on Orlando, FL, USA Jun. 27-29, 1994, New York, NY, USA, IEEE, Jun. 27, 1994, pp. 97-103, XP010122866 ISBN: 0-7803-1899-4 *p. 97-p. 98* *p. 101*.

* cited by examiner

METHOD OF DETERMINING PARAMETERS OF A SAMPLE BY X-RAY SCATTERING APPLYING AN EXTENDED GENETIC ALGORITHM INCLUDING A MOVEMENT OPERATOR

This application claims Paris Convention priority of EP 03 022 421.6 filed Oct. 7, 2003 the complete disclosure of which is hereby incorporated by reference.

BACKGROUND OF THE INVENTION

The invention relates to a method of determining parameters of a sample by X-ray scattering comprising the steps of:
 a) exposing the sample to X-rays and measuring scattered X-ray intensity;
 b) generating a parameterized model of the sample which is used for numerical simulation of scattered X-ray intensity on the basis of a physical scattering theory;
 c) comparing the experimental and simulated X-ray scattering data to generate an error value;
 d) modifying the parameters of the model by means of a genetic algorithm involving an amount of individuals each with an equal number N of encoded parameters forming a generation and applying the genetic operators of "selection", "crossover" and "mutation" used for composing successive generations of evolving individuals.

Such a method has been disclosed in A. Ulyanenkov, K. Omote, J. Harada; Physica B 283 (2000), 237–241.

X-ray analysis is applied in numerous ways in biology, chemistry, physics and materials science. The interaction of x-rays with a sample can reveal information about the sample that would be difficult to obtain by other means, if at all. Moreover, x-ray analysis is a non-destructive method, making it particularly attractive.

One way to investigate unknown parameters $t_1, \ldots t_N$ of complex samples such as multilayer structures by X-ray analysis are the so called trial and error methods. These methods start with the measurement of an experimental scattering spectrum of the sample. Then, numerous test structures (each with a different set of parameters defining a respective test structure) are assumed and simulated scattering spectra for these test structures are calculated on the basis of a physical model (e.g. kinematic scattering theory). The parameters defining the test structure whose theoretical spectrum has the best match with the experimental scattering spectrum are considered to be approximately the true parameters of the sample. The best match is typically identified as the global minimum of an error value, in particular a $\chi^2$ difference function of the experimental spectrum and the simulated spectra. Typical parameters thus approximated include film or layer thickness, lattice strain, contamination or doping level and the like.

In general, it is impossible to calculate simulated spectra for all possible test structures due to the finite capacity of computers. On the contrary, it is necessary to provide a decision algorithm determining the test structures to be calculated. There is an arbitrarily chosen test structure (or a set of test structures) to begin with, and the next test structures to be calculated are chosen by the decision algorithm on the basis of the quality of match of the previous test structures.

The most common decision algorithms are gradiental methods. If for a certain parameter $t_i$ the difference function $\chi^2$ decreases when changing the parameter $t_i$ slightly into one direction, then the next set of parameters is chosen such that $t_i$ is shifted slightly in this direction. If the difference function $\chi^2$ increases again, however, the parameter $t_i$ is no more changed into said direction. Typical gradiental methods include the Simplex algorithm, the Levenberg-Marquardt algorithm and the Newton algorithm. However, gradient methods run the risk of getting trapped in local minima not identical with the global minimum of the difference function, and no useful approximation for the true parameters of the sample can be found in such a case.

One type of decision algorithm overcoming this problem is the so called genetic algorithm. This decision algorithm works as follows:

In the beginning, there is an arbitrarily chosen starting set of so called individuals (or chromosomes). Each individual represents a test structure. These individuals all carry an equal number of so-called encoded parameters (or genes). The encoded parameters are each correlated to a physical parameter of the test structure, e.g. an impurity level or a layer thickness. Thus the number of encoded parameters corresponds to the number of physical parameters of the modeled sample to be investigated. All individuals as a whole represent a population. A typical population comprises 20 to 50 individuals.

During the genetic algorithm, the population is altered. The starting population is transformed into a new population, and this new one is altered into another one and so on. The populations at different steps of alteration are called generations. A generation to be altered is called a parent generation, and the generation newly created out of the parent generation is called an offspring generation. Thus, the starting population is the first parent generation in the algorithm. Subsequent generations of individuals are intended to contain an individual(s) approaching the global minimum of the error value.

For the creation of an offspring generation, at first the error value of each individual in the parent generation is calculated. The elite, i.e. a number of typically one or two individuals with the smallest error value in the parent generation, are copied without any alteration into the offspring generation. Then the individuals of the parent generation are subjected to genetic operators.

These operators include a selection operator which determines individuals of the parent generations which are used to produce the offspring generation.

Another operator is the mutation operator. It decides about changes in single genes of an offspring individual, in particular which genes and to what degree these genes are altered. In the state of the art, these mutations are random changes in the genes.

A third operator determines the crossover of the genes of two mating parent individuals (crossover or mating operator). It decides what gene is taken from which parent. In the state of the art, it is known to cut the parent chromosomes (=individuals) in half, and the upper part of the offspring individual is chosen as the upper part of the first parent individual, and the lower part of the offspring individual is chosen as the lower part of the second parent individual.

Through application of these genetic operators, an unlimited number of subsequent generations can be created. Typically, about 10 to 100 generations are calculated. In the final (youngest) offspring generation, the individual with the lowest error value corresponds to the test structure with the best match with the true sample structure. The genetic algorithm is very reliable and gives a good approximation to the true sample structure, with only a low risk of running into a local minimum of the error value function.

In order to increase the final accuracy of the determined sample parameters, a gradiental method may subsequently be applied, with the set of parameter determined in the genetic algorithm as a starting set of parameters in the gradiental method. This starting set of parameters should be close enough to the global minimum to avoid trapping in a non-global minimum.

However, the genetic algorithm requires a lot of calculations, determined by the amount of individuals per generation, the number of generations and the complexity of the genetic operators.

It is the object of the present invention to improve the genetic algorithm such that it can approximate the true sample parameters faster, i.e. within less generations and/or with less individuals per generation, and with better reliability.

SUMMARY OF THE INVENTION

This object is achieved by a method as described above, characterized in that a "movement" genetic operator is applied from one generation to the next to move at least some of the encoded parameters of at least some of the individuals towards respective encoded parameters of the individual with the smallest error value.

The proposed movement genetic operator is somewhat similar to the mutation operator, but the change in the gene (=encoded parameter) or genes is not random, but intentional and directed. The alteration of an encoded parameter affected by the inventive movement operator is such that the difference between the encoded parameter of the parent individual and the encoded parameter of the best matching individual of the parent generation is larger than the encoded parameter of the offspring individual and the encoded parameter of said best matching individual of the parent generation. In most cases, the inventive movement will lead to an offspring individual with a lower error value than a randomly mutated offspring individual.

The inventive movement of an encoded parameter may be set to the digital minimum, i.e. the encoded parameter is moved only one digit towards the value of the best matching individual, or it may comprise a certain percentage of the encoded parameter difference, such as 20%. Preferably, the percentage is less or equal to 50%.

It is possible to affect all or just a fraction of the individuals of a generation by the movement operator. Moreover, it is possible to alter all or only a part of the genes of an affected individual. Preferably, each affected individual is subjected to the movement operator only with respect to a few, in particular only one encoded parameter.

Note that the inventive movement operator can be applied to a parent individual immediately before creating an offspring individual, or directly at the creation of the offspring individual.

In a particularly preferred variant of the inventive method, after a given number k of successive generations the genetic operator of "mutation" is no longer applied in evolution of further generations.

In other words, in the last few generations calculated, the mutation genetic operator is deactivated. By this means, random changes in the genes are avoided when the encoded parameters and the respective test structure are already close to the corresponding desired true structure. During creation of the last generations, random changes most often worsen the quality of match of the corresponding test structure and lead away from the wanted global minimum of the error value function.

When dispensing with the random changes during the last generations in accordance with the invention, the exact global minimum can be approximated by the genetic algorithm with a higher accuracy, since only genes already close to this minimum are available for new combinations in the offspring generations. The inventive genetic algorithm during the last generations can replace a subsequent application of a gradiental method and thus save calculation power and time.

When a total number of G generations is created by the inventive genetic algorithm, and after k generations the mutation operator is no more applied, then k may be chosen such that a minimum number of generations G−k is performed without the mutation operator, for example with G−k≧5, or such that a minimum fraction of generations (G−k)/G is performed without the mutation operator, for example (G−k)/G≧20%. Alternatively or in addition, it is also possible that the transition generation (i.e. the determination of k) can be coupled to a minimum quality of match of the best fitting individual of the transition generation: as soon as the quality of match of the best fitting individual of a generation reaches a limiting value, subsequent generations are generated without the mutation operator.

In a preferred variant, at least some of the offspring individuals of every successive generation evolve from more than two parent individuals of the respective previous generation. In particular, genes from three parent individuals can be combined to generate a new offspring individual. By this means, the genes of selected individuals can be mixed in less generations, and a wider parameter space can be explored.

Further preferred is a variant of the inventive method, wherein at least some of the offspring individuals of every successive generation evolve from only one parent individual of the respective previous generation (="cloning"). Genetic operators such as mutation and movement may still apply, however. Thus, successful gene combinations can be kept even when they do not belong to a kept elite, and can be slightly changed with a high chance of being an individual of low error value in the offspring generation again.

In an alternative and advantageous variant of the inventive method, the "crossover" genetic operator is modified such that the encoded parameters of each offspring individual is selected randomly from the respective encoded parameters of the parent individuals of the previous generation. The vector describing the random selection of the parent individual for each gene is called the random chromosome. The random choice of the genes accelerates the mixing of selected successful genes and promotes the exploration of a wide parameter space.

It is particularly advantageous for a variant if from one generation to the next at least the individual with the smallest error value is transferred unchanged (="elite"). By this means the individual with the lowest error value in the offspring generation always has a lower or equally low error value as the individual with the lowest error value in the parent generation. Therefore the matching of the best matching individuals can only improve in the course of the generations.

A preferred variant of the inventive method provides that the error value is generated by means of a weighting function, in particular based on logarithmic values of the scattering data. By means of the logarithmic scale, an overestimation of regions of high absolute values in the error value function is avoided. The weighting function is preferably a logarithmically scaled instead of absolute x-ray intensity within the $\chi^2$ difference function.

Further advantages can be extracted from the description and the enclosed drawings. The features mentioned above and below can be used in accordance with the invention either individually or collectively in any combination. The embodiments mentioned are not to be understood as exhaustive enumeration but rather have exemplary character for description of the invention.

The invention is shown in the drawings:

DESCRIPTION OF THE PREFERRED EMBODIMENT

Figure 1:
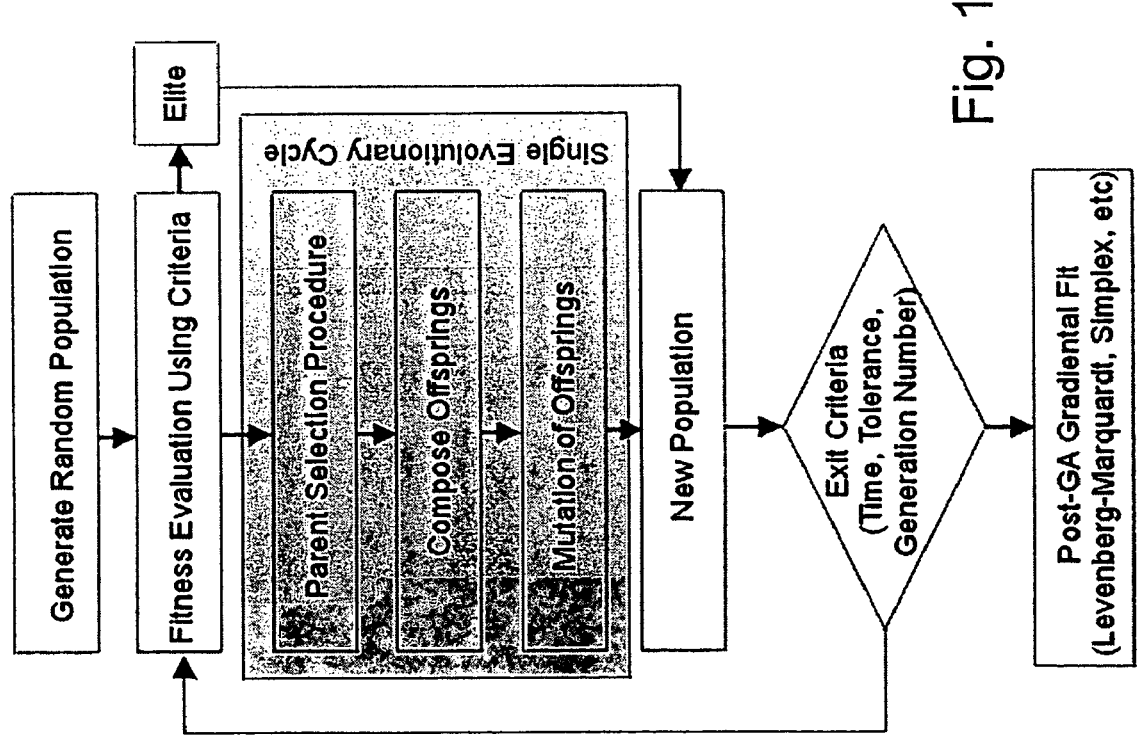
FIG. 1 shows a flowchart of a genetic algorithm (=CGA, Classical GA) according to the state of the art.

In the following, the inventive extended genetic algorithm and its application to x-ray analysis are explained in detail.

The classic scheme of genetic algorithm is extended to improve the robustness and efficiency of the method. New genetic operators implemented in this work are shown to increase the convergence speed and reliability of the optimization process. A complex model function with multiple local extrema and real x-ray reflectivity and diffraction data have been used to testify the modified algorithm. The effectiveness of the new technique is compared to other optimization methods.

X-ray metrological methods in science and industry have been proved to be efficient techniques for sample characterization and growth process development and control. A large variety of sample structures can be probed by x-rays to examine film thickness, interface roughness, crystallographic lattice strain and distortion, material contamination, etc. Although the measured x-ray data can be used directly for evaluation of some sample parameters, the detailed knowledge about the sample structure can only be obtained using special data treatment procedures. These procedures usually utilize a trial-and-error technique, which uses a parameterized sample model for the simulation of the x-ray scattering process, and then the difference $\chi^2$ between calculated and measured intensities is minimized in view of the sample parameters. Thus, an effective and robust optimization algorithm is required for accurate data interpretation. Moreover, in most of experimental setups, x-ray measurements provide the magnitude of scattered x-ray intensity, whereas the amplitude and the phase of x-rays are lost, and that is why no procedures are available for reconstruction of sample physical parameters directly from measured intensities. The loss of x-ray phase information during the measurements causes the ambiguity of data interpretation results, e.g. when several sample models result in a comparably small difference $\chi^2$ between measurements and simulations. This situation requires from the optimization technique to be able to find not only a single global minimum, but also a set of deepest minima on the $\chi^2$ hypersurface, which may contain real physical solutions. Genetic algorithms (=GA) [Ref. 1], widely used nowadays, seem to be most successful in solving all mentioned problems in x-ray data analysis. They combine a stochastic search and strategy aimed features that help to find the global minimum along with other local minima of the cost function $\chi^2$ of comparable magnitude.

In the present work, we propose specific modifications of the classic GA scheme, which improve the efficiency of the algorithm. These new implementations into standard GA have been testified and the results are compared with results obtained by classic GA (CGA). As the test objects, a complex model function possessing multiple minima, and real x-ray diffraction and reflection measurements have been used. We describe and qualitatively ground the implemented modifications of the genetic algorithm. Test results of the proposed method are presented called further extended GA (XGA) for model multi-minima function and the comparison with CGA. The real x-ray diffraction and reflection measurements are fitted by using extended GA and various methods, and the performance of XGA is compared with other optimization techniques [Ref. 4].

An explanation of the details of genetic algorithms can be found in numerous publications (see, e.g. [Ref. 1] and citations therein), and in this section only the principle construction of a classic GA is described. Genetic algorithms exploit the Darwin's evolutionary idea and the principle of survival of most adapted individuals in a population. The first step in any GA application is the formalization of the parameters to be investigated in order to unify all the operations with them. Usually, the binary representation of the whole parameter space is used, that allows to easily code the problem. Every point in the parameter space then represents a unique physical state of the investigated system, and the goal is to explore this space to find the point which gives the best fit according to the pre-defined fitness criteria. Since the fitted-parameters are formalized, any set of them comprehensively describing the system is considered as an individual; the limited number of individuals compose a population, which is evolving on the basis of some genetic rules. The procedure of parameter formalization is called encoding, whereas reverse operation of obtaining the physical parameters is a decoding.

The typical GA search procedure consists of the following steps, depicted in FIG. 1. Firstly, the random population of individuals, which are the points in the parameter space or, the same, the single set of the system fitted parameters, is created (the size of the population is an internal GA parameter). Then the population begins to evolve by the production of new generations, i.e. the creation of the successive populations on the basis of the primary one. The most principle rules (called also GA operators) used for the creation of a new generation of individuals are selection of parents, crossover and mutation operators. The first operator regulates the parents selection procedure for the production of offsprings for the new generation. The second rule describes how the parents hand down their features (single parameters, genes) to children. The mutation operator provides irregular changes of offsprings to strengthen a statistical nature of GA. Applying these basic operators along with other optional rules (for example, elitism, i.e. the transfer of the fittest individuals from the current generation to the successive generation without any changes), after a certain number of generations GA delivers the fittest individual, i.e. the set of parameters at which the system satisfies the fitness criteria in the best way. The probability to find the best existing set of parameters by GA increases with the number of generations evolved, i.e. with the length of evolution.

All of the operators described above have various implementations and internal parameters, which are used to optimize the GA efficiency for different applications. The genetic algorithm, being correctly tuned for the concrete problem, demonstrates excellent results as an optimization and search procedure [Ref. 2]. In this work, we propose further modifications of basic GA operators and general rules to increase the efficiency and reliability of the algorithm. These modifications are:

[1.] One more basic GA operator is implemented, the movement operator. Before the selection of parent individuals for mating, a limited number of parents are moved towards the best individual in the population, i.e. the parameters of the moved parents are changed closer to the parameters of the fittest individual. This operator improves the convergence of GA, by increasing the amount of individuals in the vicinity of the fittest one.

[2.] Each offspring can have not only two parents but arbitrary number of parents. In our case, we particularly propose a number of parents n=1, 2, 3. This multiple choice combines the classic two-parental approach with single "cloning" (n=1) of parents, which improves the convergence of GA by increasing an amount of individuals with better fitness, and multi-parental options (n=3), which increase the variety of a population by wider exploration of the parameter space.

[3.] A new crossover principle, providing a better mixture of parents' features in children, is implemented by using a random sequence of bits, the so called random chromosome. When parents mate, the offspring inherits the parameter from that parent, to which the corresponding bit in the random chromosome points to. This modification results in a more efficient parameter mixture in the crossover procedure, optimizes the source code and accelerates the algorithm because only simple boolean operations are involved (in particular in the case of two parents).

[4.] A more effective principle for the formation of new generations is developed. The sequence of formation is the following: firstly, the limited number of elite individuals is moved to the successive population; then the population is filled by the individuals from the previous generation and by new offsprings randomly, with a probability depending on the individual's fitness and the number of children left. This improvement prevents individuals with good fitness from being replaced by new children and replaces the individuals with rather bad fitness, i.e. increasing the convergence and decreasing the probability for the best solutions to be skipped.

[5.] The mutations are forbidden in a given number of last generations. This modification permits to use solely GA for a fine parameter fitting cycle. Because of their stochastic nature, conventional GA schemes rarely deliver exactly the point with the best fitness in the parameter space. Usually, the gradiental optimization methods have to be further applied in the vicinity of the solution found by GA to refine the parameters [Ref. 2] (see flowchart in FIG. 1). For example, if the fitness criterion is based on some cost function (typically, the difference between experimental and simulated data), and the aim of GA is to find the global minimum of this cost function, the final solution is usually found by GA near this minimum point. A gradiental method like Levenberg-Marquardt has to be used to "slide down" the solution onto the bottom of the function $\chi^2$. Our fifth modification allows to precisely localize the final solution with an accuracy suitable for data interpretation, which reduces the overall optimization time in comparison with the cascade use of GA and gradiental techniques.

Figure 2:
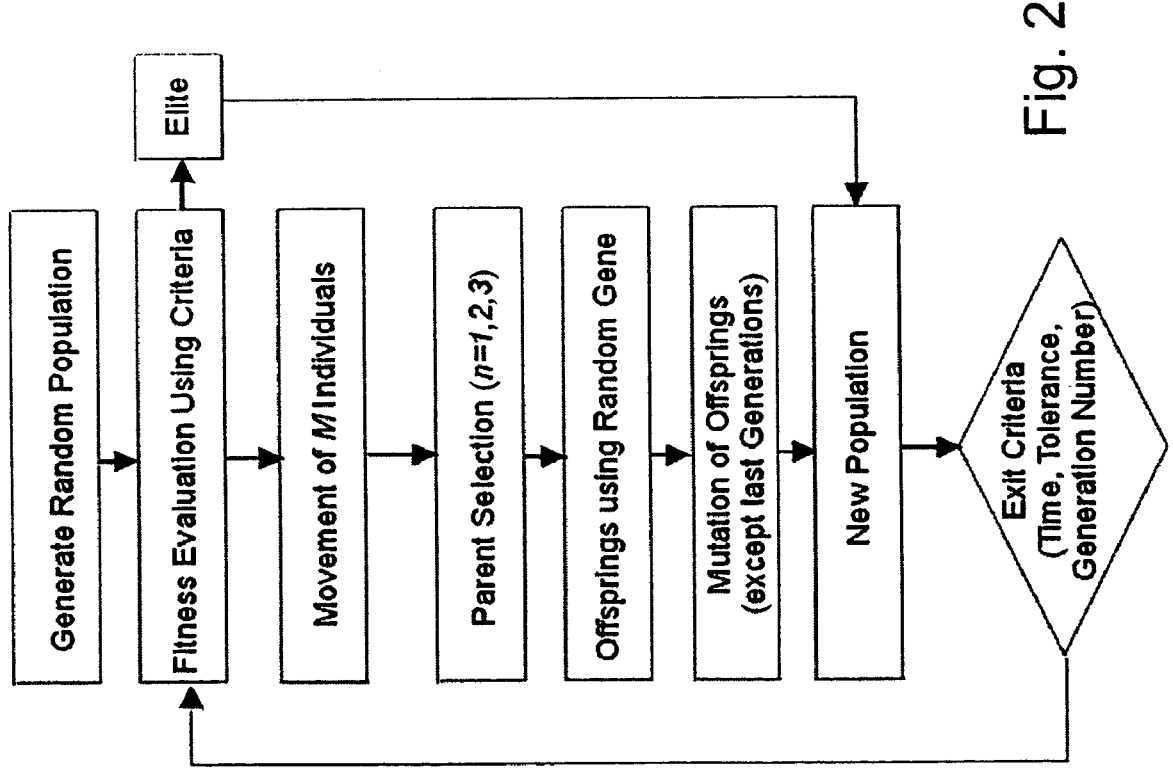
FIG. 2 shows a flowchart of an inventive extended genetic algorithm (=XGA)

Thus, our modified XGA version of genetic algorithm has the following principle scheme (flowchart in FIG. 2):
(i) generation of a random population consisting of S individuals (population size);
(ii) evaluation of fitness;
(iii) movement of M individuals towards the fittest one;
(iv) creation of C children by using one parent ($p_1$, cloning), two parents ($p_2$, crossover through random gene), and three parents ($p_3$), $C=p_1+p_2+p_3$;
(v) if mutations are permitted in current generation, m mutations of parameters are carried out, reach being an inversion of a random bit in an corresponding children's parameter;
(vi) a new population is created.

To optimize a source code, the new generation is constructed on the basis of the previous one, firstly by selection of unchangeable elite E individuals, then by substitution of old individuals by C children in dependence on the fitness of replaced individuals and the number of remained children. The evolution proceeds by repeating the cycle in FIG. 2 either G times (number of generations) or until a requested fitness tolerance is reached. In the last F generations, the mutations are forbidden to refine the fit results.

Figure 3:
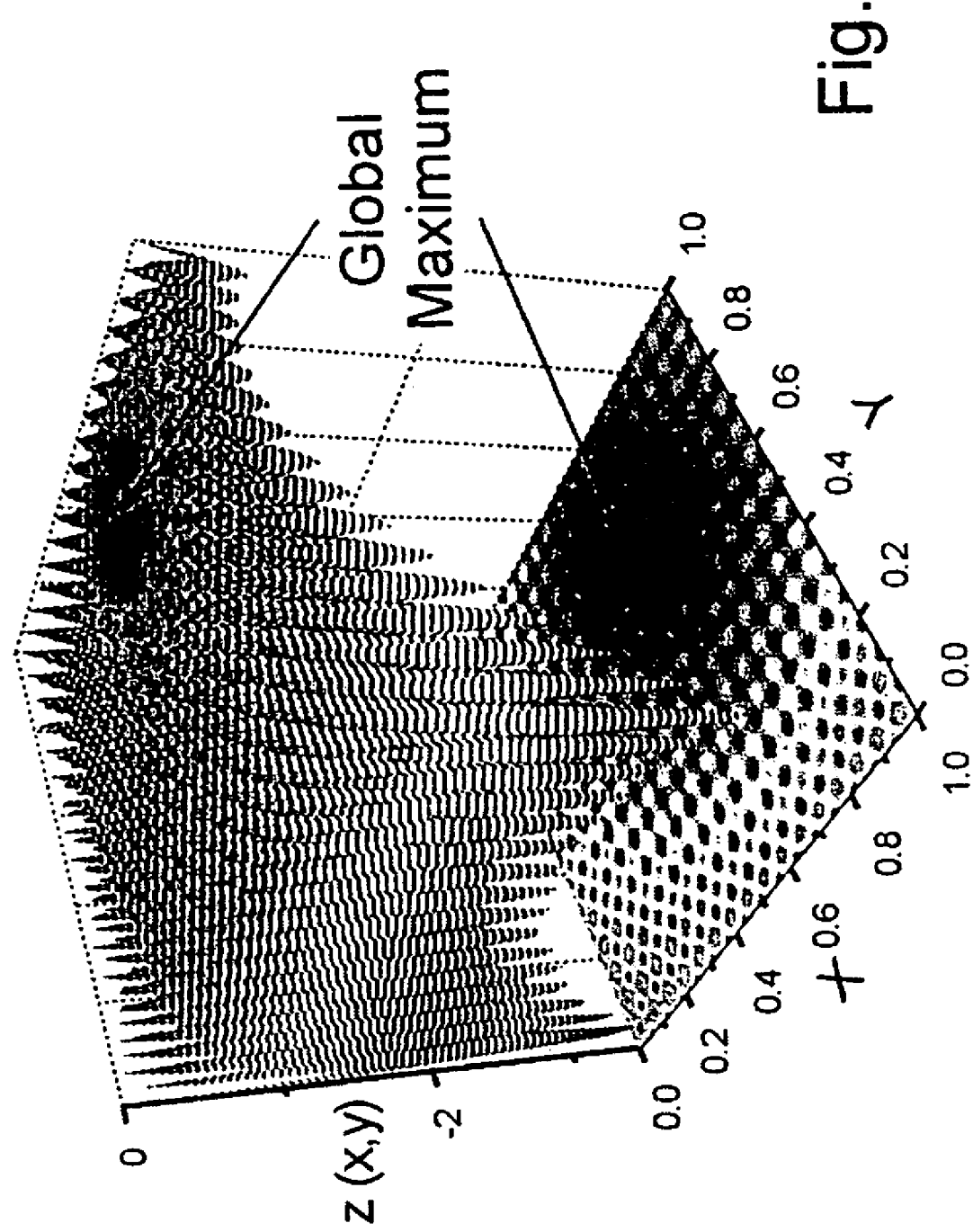
FIG. 3 shows a graphic representation of an analytical function used to test the inventive method, the model function having numerous local maxima along with a hardly recognizable global one.

To study an effectiveness of above-mentioned XGA implementations, we used firstly a smooth two-dimensional analytical function $$z(x,y)=-[(x-0.75)^2+(y-0.625)^2]*[2-\cos(100(x-0.75))-\cos(100(y-0.625))]$$

possessing single global maximum at (x;y)=(0.75; 0.625) and multiple local maxima (FIG. 3); the function is defined within the interval [x;y]=[0 . . . 1; 0 . . . 1].

Figure 4:
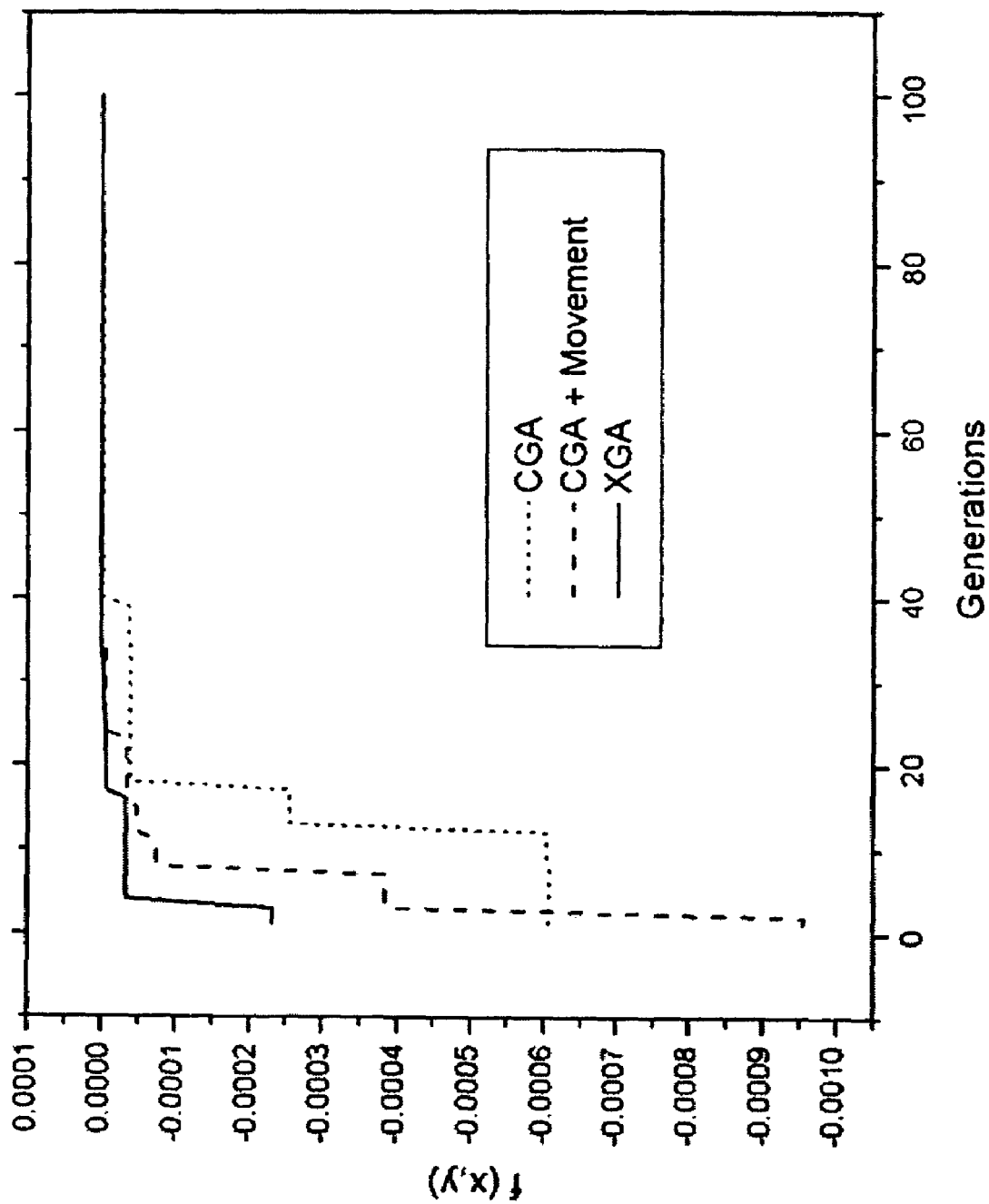
FIG. 4 shows a convergence chart for the CGA, CGA+ movement operator, and XGA for the analytical function of FIG. 3.

FIG. 4 shows the convergence diagram for CGA, CGA with only movements, and full-featured XGA. Evidently, XGA finds global maxima faster than other modifications at equal conditions (the population consists of 200 individuals). We also carried out the tests with a more complicated model function, viz. linear combination of several functions similar to the depicted one in FIG. 3, but with different values of the constants. Then the statistical error of trapping in the wrong maxima has been evaluated for CGA and XGA by performing multiple runs of both algorithms. The error for CGA is found to be 28% against 4% for XGA, and thus XGA demonstrates higher reliability in comparison with a classic GA scheme.

Figure 5:
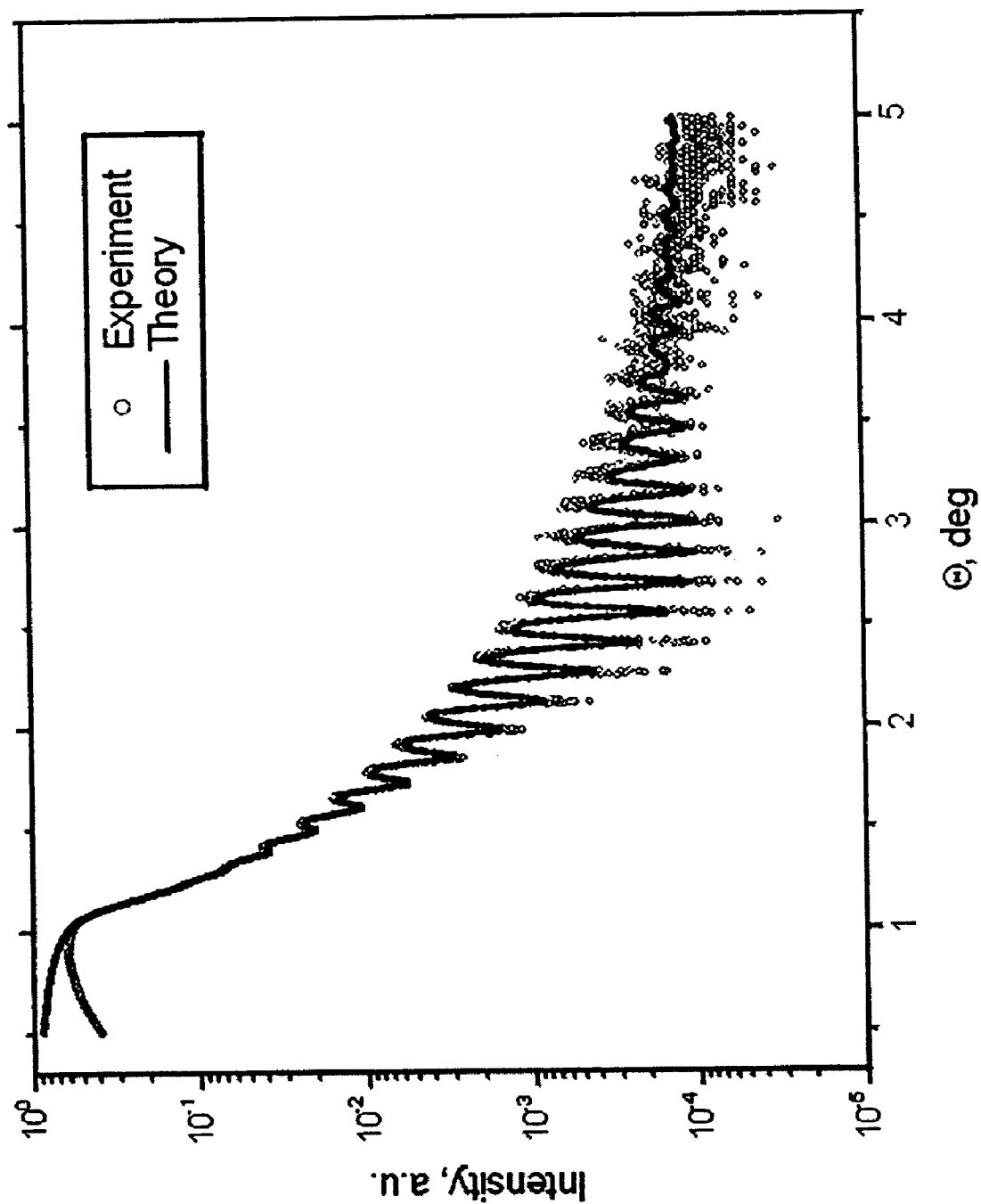
FIG. 5 shows an X-ray reflectivity diagram of a Au/Fe$_3$O$_4$/MgO sample, with experimental results dotted and XGA simulation results as a continuous line.
Figure 6:
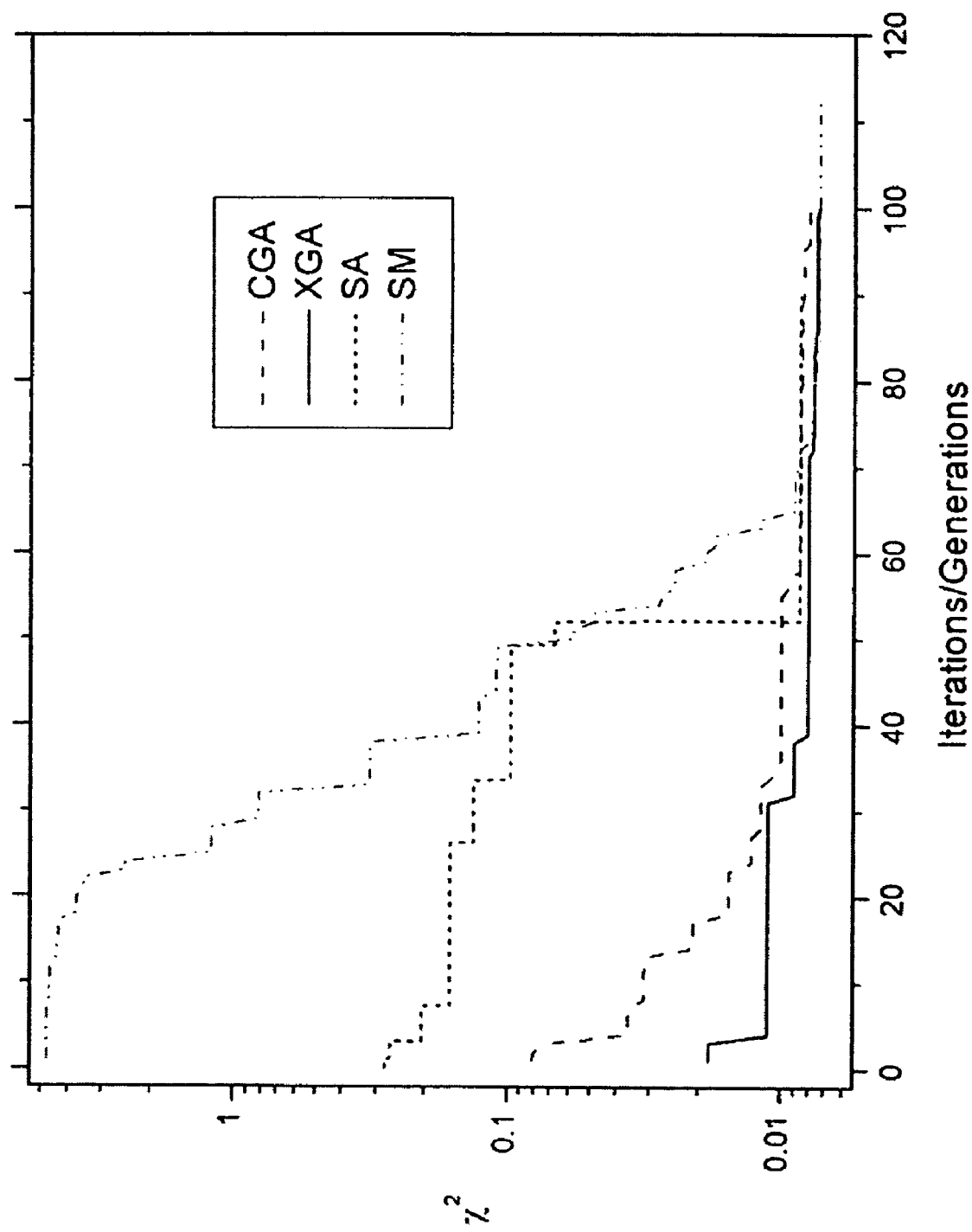
FIG. 6 shows the convergence of the $\chi^2$ function for CGA, XGA, Simulated Annealing and Simplex Method when fitting the experimental x-ray reflectivity data of FIG. 5, wherein the iteration scale of Simulated Annealing and Simplex Method techniques is reduced to the GA generations scale on the principle of equal computation time.

XGA has been also applied for the fitting of real experimental data from x-ray reflectivity (XRR) and high-resolution x-ray diffraction (HRXRD), the two most commonly used x-ray techniques. The convergence and speed of XGA are compared with other known methods, simulated annealing (SA) and the simplex method (SM). FIG. 5 shows measured (open dots) and simulated (solid lines) x-ray reflectivity from gold and magnetite thin solid films on MgO substrate at a wavelength $\lambda$=0.154056 nm. The sample model consisting of the sequence Au/Fe$_3$O$_4$/MgO with the nominal thicknesses 55 nm/120 nm/substrate and some roughness at the interfaces between the layers has been used for fitting of reflectivity data simulated by Parratt's formalism [Ref. 3] to the measured curves. The fitted parameters were the thicknesses of the layers $t_{Au}$ and $t_{Fe3O4}$ and the roughnesses of the sample surface and the interfaces. All the methods (CGA, SA, SM, XGA) resulted in an acceptable fitness of curves with slight differences in the refined parameters which, however, are within the precision of experimental data. The values of the thicknesses and roughnesses are found to be $t_{Au}\cong 53.8$ nm, $t_{Fe3O4}\cong 146.3$ nm, $\sigma_{surf}\cong 0.78$ nm, $\sigma_{Au/Fe3O4}\cong 0.1$ nm, $\sigma_{Fe3O4/MgO}\cong 0.3$ nm. However, the effectiveness of the methods is evidently different, as follows from the FIG. 6 showing the $\chi^2$ convergence diagrams for each used technique. To adjust the time scales of algorithms, the iteration scales of SA and SM are brought into correspondence to GA's generations scale by multiplying them by the ratio of computation times $t_{GA/SA}$ and $t_{GA/SM}$. Diagrams show that XGA finds the best available solution faster than the other methods. FIG. 6 demonstrates also the advantage of XGA due to the fifth implementation from the Section II, i.e. the prohibition of mutation in the final stage of evolution. After 100 generations, CGA is still localized in the vicinity the global minimum of $\chi^2$, whereas XGA has already found the point, recognized by simplex method as an exact global minimum (with certain tolerance), due to ban of mutations after the 60th generation. Thus, gradiental methods must not be used to refine a fit.

Figure 7:
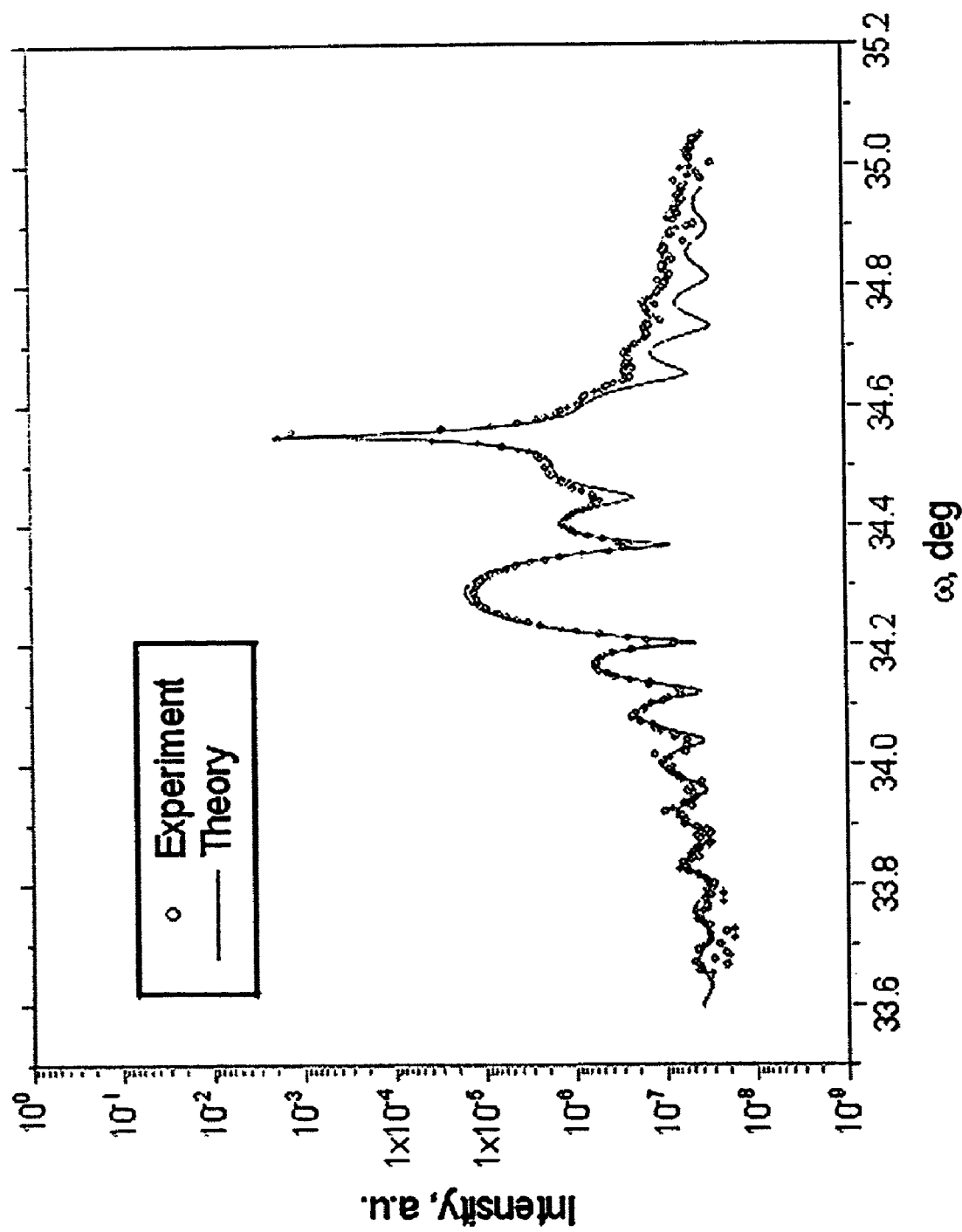
FIG. 7 shows an X-ray diffraction diagram of a Si$_{1-x}$Ge$_x$/Si(004) Bragg reflection diagram, with experimental results dotted and XGA simulation results as a continuous line.
Figure 8:
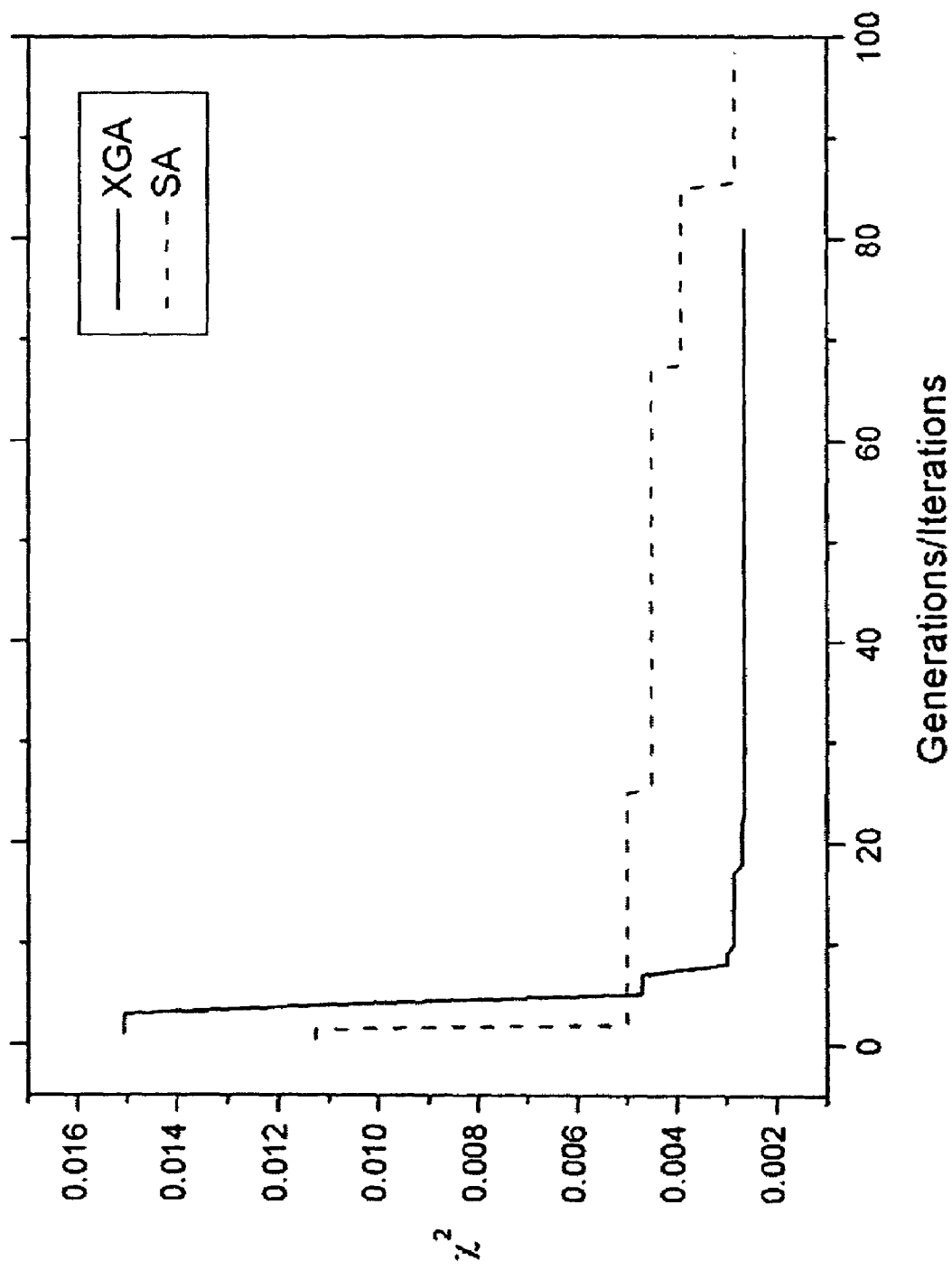
FIG. 8 shows the convergence of the $\chi^2$ function for XGA and Simulated Annealing when fitting the experimental x-ray diffraction data of FIG. 7, wherein the iteration scale of the Simulated Annealing method is reduced to the GA generations scale on the principle of equal computation time.

X-ray diffraction measurements (open dots) from a Si$_{1-x}$Ge$_x$/Si (004) Bragg reflection at wavelength $\lambda$=0.154056 nm are shown in FIG. 7. Two parameters, the thickness of the Si$_{1-x}$Ge$_x$/Si layer and the concentration of germanium x, have been fitted (solid line in FIG. 7). The discrepancy between the curve simulated by dynamical diffraction theory and the experimental data on the right wing of the substrate peak are caused by a diffuse x-ray scattering, which is not taken into account in the present calculations. Both SA and XGA methods used for minimization of the $\chi^2$ function lead to close values of thickness $t_{SiGe}\cong 65.7$ nm and concentration $x\cong 9.2\%$. However, the $\chi^2$ convergence charts in the FIG. 8 clearly demonstrate the advantage of XGA in speed (SA iterations are resealed by time ratio factor).

The inventive extended genetic algorithm is shown to be the most effective and robust optimization technique in comparison with the classic genetic algorithm, simulated annealing and the simplex method. Phenomenological tests with complex model functions possessing multiple extrema, as well as with real experimental x-ray data, both reflectivity and diffraction, have shown the advantages of XGA. In view of large computer resources required for fitting of x-ray data, the robustness and quickness of XGA plays an essential role for precise data analysis in x-ray analytical software.

REFERENCES

[Ref. 1] D. E. Goldberg, Genetic Algorithms in Search, Optimization and Machine Learning, Addison-Wesley, Reading, Mass., 1989.
[Ref. 2] A. Ulyanenkov, K. Omote, J. Harada, Physica B 283 (2000) 237.
[Ref. 3] L. G. Parratt, Phys. Rev. 95, 359 (1954)
[Ref. 4] F. H. Walters, L. R. Parker, S. L. Morgan and S. N. Deming, Sequential Simplex Optimization, CRC Press, Boca Raton, Fla., 1991; H. L. Aarts and J. Kost, Simulated Annealing and Bolzman Machines, John Wiley, New York, 1989

We claim:

1. A method for determining parameters of a sample by X-ray scattering, the method comprising the steps of:
   a) exposing the sample to X-rays and measuring scattered X-ray intensity;
   b) generating a parameterized model of the sample which is used for numerical simulation of scattered X-ray intensity on a basis of a physical scattering theory;
   c) comparing experimental and simulated X-ray scattering data to generate an error value;
   d) modifying parameters of the model by means of a genetic algorithm involving a number of individuals each having an equal number N of encoded parameters and forming a generation, and applying genetic operators of "selection", "crossover" and "mutation" to compose successive generations of evolving individuals, wherein a "movement" genetic operator is applied from one generation to the next which moves at least some of the encoded parameters of at least some of the individuals towards respective encoded parameters of an individual having a smallest error value.

2. The method of claim 1, wherein the genetic operator of "mutation" is no longer applied in evolution of further generations after a given number k of successive generations.

3. The method of claim 2, wherein at least some offspring individuals of each successive generation evolve from more than 2 parent individuals of a respective previous generation.

4. The method of claim 1, wherein at least some offspring individuals of each successive generation evolve fmm only 1 parent individual of a respective previous generation (="cloning").

5. The method of claim 1, wherein the "crossovers" genetic operator is modified such that encoded parameters of each offspring individual are selected randomly from respective encoded parameters of parent individuals of a previous generation.

6. The method of claim 1, wherein at least one individual with a smallest error value is transferred unchanged (="elite") from one generation to a next.

7. The method of claim 1, wherein an error value is generated by means of a weighting function.

8. The method of claim 7, wherein said weighting function is based on logarithmic values of the scattering data.

* * * * *